United States Patent [19]
Jensen et al.

[11] 4,023,607
[45] May 17, 1977

[54] POLYETHYLENE URINE BAG WITH TUBE

[75] Inventors: Ole Roger Jensen, Copenhagen N.; Preben Kobbero, Brondby Strand, both of Denmark

[73] Assignee: Automaticon A/S, Denmark

[22] Filed: June 2, 1975

[21] Appl. No.: 583,179

[30] Foreign Application Priority Data

June 7, 1974  United Kingdom ............ 25467/74

[52] U.S. Cl. .................................................. 150/1
[51] Int. Cl.² ........................................ B65D 33/00
[58] Field of Search ...................................... 150/8, 1

[56] References Cited

UNITED STATES PATENTS

| 3,173,579 | 3/1965 | Curie | 150/8 UX |
| 3,537,109 | 11/1970 | Spurrier | 150/8 X |
| 3,583,460 | 6/1971 | Faust | 150/8 |
| 3,690,524 | 9/1972 | Haberhauer | 150/8 X |
| 3,915,212 | 10/1975 | Bujan | 150/8 |

*Primary Examiner*—Donald F. Norton
*Attorney, Agent, or Firm*—Brucknam and Archer

[57] ABSTRACT

A bag made of two layers of film material welded together along their edges except at an aperture in which is inserted one end of a tube of the same material as the bag, the entire circumference of said tube being tightly sealed to the sides of the bag aperture by heat welding.

1 Claim, 2 Drawing Figures

POLYETHYLENE URINE BAG WITH TUBE

The invention relates to a bag such as a urine bag of polyethylene film consisting of two layers of film welded together along their edges except at an aperture in the upper edge, in which aperture one end of a cylindrical or oval tube of the same material is inserted. The invention also relates to a method of producing the bag.

Bags of impressed PVC-film are already known. In these known bags tightness is established between the tube, which is also made of PVC, and the layers of film surrounding it in the aperture by means of high frequency welding, but for technical resons this sealing method cannot be applied to polyethylene film, which material is more advantageous for these bags than PVC, among other things because of its lower weight and lower price per weight unit, because it can inexpensively be provided with print, and because even very thin film can be used. For these reasons bags made of two layers of polyethylene film have been extensively used, said two layers being, even though they may be quite thin (normally under 0.1 mm), welded together along their edges by heat welding. However, as it has so far been impossible by means of the known heat welding methods to provide a tight seal between the layers of film (no matter if they are made of PVC or polyethylene) and a tube along its entire peripheral surface, a tube has been used, one end thereof being secured to a conic connecting piece provided with outer ribs, said connecting piece being pressed down into the bag aperture and frictionally retained therein. It has, however, also been suggested to use connecting pieces or mouthpieces of a rigid plastic material carrying on their lower portion two wings being situated diametrically opposed in a plane through the longitudinal axis of the mouthpiece and welded together with the bag wall. In order to avoid the use of the relatively expensive connecting pieces it has further been suggested to secure a PVC-tube direct in the aperture by causing it to expand radially upon the insertion. This expansion may be caused by dipping the tube into a swelling agent before passing it through the aperture, whereafter the end portruding into the bag will expand and prevent withdrawal of the tube.

However, this process is also rather timeconsuming and may involve difficulties, thus reducing the advantages of using the quick welding method. Consequently, it is an object of the present invention to provide a bag, which can be made more quickly and at lower costs than the known ones, and which may conveniently be made with an effectively sealed joint between the film material in the aperture of the bag and the peripheral surface of the tube. Further it is an object of the invention to provide a method for the production of the bag.

The bag according to the invention is characterized in that the connection between the entire circumference of the tube and the sides of the bag aperture is produced in liquid and airtight condition by heat welding including impulse welding.

According to the invention the bag can be produced by a method which is characterized in that the bag of plastic film and the tube - both being of the same material such as polyethylene - are joined by merely using heat welding, possibly in the form of impulse welding, the heat welding between the entire peripheral surface of the tube and introduced into the bag aperture and the side walls of the aperture being performed between two heated welding jaws being protected by a material preventing adherence of the film to the jaws, said welding jaws being so shaped that when moved towards each other they surround an aperture having a circumference which is smaller than the circumference of the tube portion with the surrounding layers of film inserted into said aperture, whereby the tube will be somewhat compressed when the jaws meet, and the material laterally to the middle-line plane situated in the direction of motion of the jaws will move towards the side surfaces of the aperture amd be pressed against the wall of the aperture along the entire surface of said wall.

The side walls of the aperture are preferably evenly curved all the way round, and the diameter perpendicular to the direction of motion of the welding jaws is preferably a little bigger than the outer diameter of the tube.

This arrangement, in which the tube is pressed outwards towards the portions, where the jaws meet by the pressure of the jaws, eliminates the risk that the edges between the plane surfaces of the jaws and the recesses forming said aperture spoil the thin plastic film during the closing movement, and the tight abutment of the film all round the tube prevents the normal difficulties by obtaining a tight joint all round, also in the plane where the jaws meet.

The invention will now be described in detail with reference to the drawing, in which.

Figure 1:
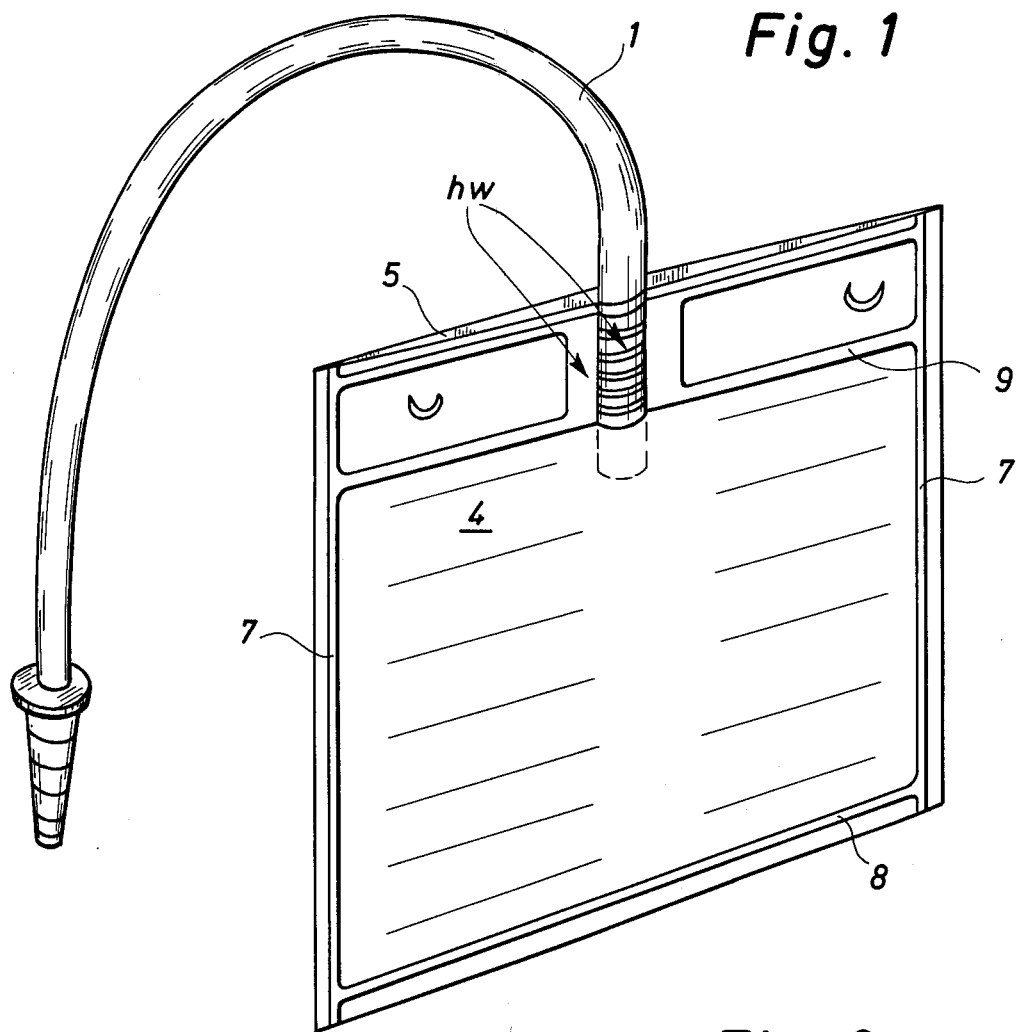
FIG. 1 shows an embodiment of the bag according to the invention.

The bag shown in FIG. 1 comprises two films 4 and 5 being welded together by heat welding along side seams 7, a bottom seam 8, and a top seam 9, the latter, however, having an aperture in which a tube 1 is inserted, the portion of said tube inserted in the aperture of the welding seam at the entire circumference being welded to the films 4 and 5 by heat welding as indicated by the arrows hw.

Figure 2:
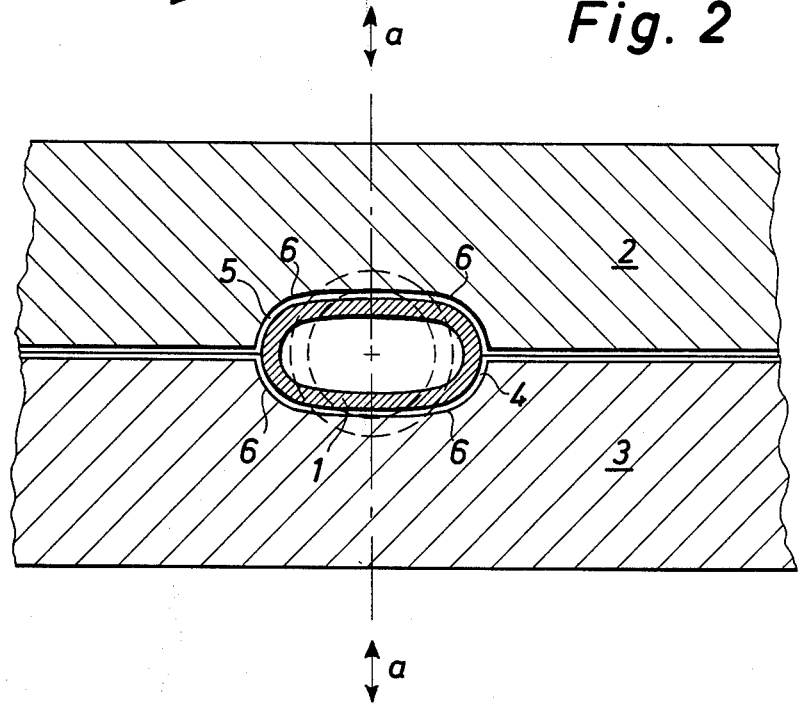
FIG. 2 shows the shape of a pair of welding jaws in an apparatus, whereby the method according to the invention can be carried out.

The welding jaws shown in FIG. 2 are intended for welding a tube of circular cross section, but it should be understood that the tool may just as well be designed in such a way that it can be used for tubes having for example oval or polygonal cross sections. Normally, however, circular cylindrical tubes are preferred as the tool will thus be the simplest possible.

A tube 1 of a polyethylene material is shown in dotted lines in its original form, whereas in full lines it is shown in the form assumed when a pair of heat welding jaws 2 and 3, respectively, are closed tightly around the tube 1. The tube is surrounded by two films 4 and 5, respectively, forming the side walls of the bag by heat welding, said films being connected all the way round except at the portion where the end of the tube 1 is inserted into the bag, it will be seen that the aperture between the jaws has curved corners 6 having a big radius of curvature. It will be understood, however, that the aperture may have no actual corners, its walls consisting of evenly curved walls, the radii of curvature of said walls in the direction of motion of the jaws 2 and 3 indicated by the double arrows a being bigger than the radii of curvature of the plane perpendicular hereto. By using tubes of different cross sections, such as oval or polygonal ones, the aperture between the jaws can without difficulty be formed correspondingly, and in such a way that it has a wall having radii of curvature varying evenly in the circumferential direction.

When the welding jaws 2 and 3 are moving towards each other the tube 1 will be somewhat compressed in the direction of their motion, and the tube material and the parts of the films 4 and 5 situated laterally to the diameter plane in the direction of motion will yield and be pressed outwards so as to abut closely on the sides of the aperture all the way along the peripheral surface. The jaws 2 and 3 being heated to the welding temperature, a uniform, tightly sealed joint between the films 4 and 5 and all the way round the exterior of the tube 1 will be obtained.

It will be understood that the welding jaws 2 and 3 may be formed in such a way that such a length of the tube may be inserted between the jaws that during the heat welding welding seams are produced, extending further down the bag than the tube. Such welding seams can be applied to the forming of a check valve preventing urine or other liquid from flowing out of the bag.

The invention makes it possible to produce a completely tight bag which only consists of e.g. polyethylene material and which can be made very quickly. For example bags of this type, manufactured by heat welding, can be made in numbers about three times as great per time unit as bags joined by high-frequency welding, and the fixing of the tube by heat welding does not only provide better securing than the known methods, but also saves time and reduces waste.

We claim:

1. A bag such as a urine bag consisting of two layers of film of polyethylene directly welded together along their edges except at an aperture in the upper edge, in which aperture one end of a tube of the same material is inserted, characterized in that the connection between the entire circumference of the tube and the sides of the bag aperture is produced in liquid and airtight condition by heat welding including impulse welding, the thickness of each layer of film being less than 0.10 mm.

* * * * *